(12) United States Patent
Windheuser et al.

(10) Patent No.: US 12,075,991 B2
(45) Date of Patent: Sep. 3, 2024

(54) TISSUE ACQUISITION HELIX DEVICE

(71) Applicant: BOSTON SCIENTIFIC SCIMED, INC., Maple Grove, MN (US)

(72) Inventors: Kevin Windheuser, Hopkinton, MA (US); Juan Pablo Ortiz Garcia, Heredia (CR); Rosa Angelica Perez, Heredia (CR); Yeison Calvo, San Ramon (CR); Christopher R. Deuel, Melrose, MA (US); Kevin L Bagley, Dedham, MA (US); Shaun Dennis Comee, Fiskdale, MA (US); Steven Jimenez Bustamante, San Ramon (CR)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 516 days.

(21) Appl. No.: 17/089,632

(22) Filed: Nov. 4, 2020

(65) Prior Publication Data

US 2021/0128126 A1    May 6, 2021

Related U.S. Application Data

(60) Provisional application No. 62/930,700, filed on Nov. 5, 2019.

(51) Int. Cl.
 *A61B 10/04* (2006.01)
 *A61M 25/00* (2006.01)

(52) U.S. Cl.
 CPC ........ *A61B 10/04* (2013.01); *A61B 2010/045* (2013.01); *A61M 2025/0095* (2013.01)

(58) Field of Classification Search
 CPC .............. A61B 10/04; A61B 2010/045; A61B 17/00234; A61B 17/0469; A61B 17/0625; A61B 2017/00292; A61B 2017/0034; A61B 2017/00349; A61B 2017/06047; A61B 2017/0609; A61B 2090/0807; A61B 90/08; A61M 2025/0095
 See application file for complete search history.

(56) References Cited

U.S. PATENT DOCUMENTS

| | | | | |
|---|---|---|---|---|
| 4,209,019 A | * | 6/1980 | Dutcher | A61N 1/056 607/127 |
| 4,381,013 A | * | 4/1983 | Dutcher | A61N 1/056 607/128 |
| 5,003,992 A | * | 4/1991 | Holleman | A61N 1/0575 600/377 |

(Continued)

FOREIGN PATENT DOCUMENTS

| | | | | |
|---|---|---|---|---|
| EP | 2203201 B1 | * | 5/2018 | ........ A61M 25/0084 |
| WO | 2020117920 A1 | | 6/2020 | |

OTHER PUBLICATIONS

International Search Report and Written Opinion dated Feb. 12, 2021 for International Application No. PCT/US2020/058973.

*Primary Examiner* — Rene T Towa
(74) *Attorney, Agent, or Firm* — Seager, Tufte & Wickhem, LLP

(57) ABSTRACT

A tissue grasping device for use with an endoscope may include a sheath, a control wire slidably disposed within the sheath, and a helical coil disposed over and attached to the control wire. The helical coil may include a proximal region in which adjacent windings are in contact, and a distal region in which adjacent windings are spaced apart. The helical coil may have a sharpened distal tip.

17 Claims, 19 Drawing Sheets

(56) References Cited

U.S. PATENT DOCUMENTS

| | | | | |
|---|---|---|---|---|
| 5,261,419 | A * | 11/1993 | Osypka | A61N 1/0573 607/122 |
| 5,456,708 | A * | 10/1995 | Doan | A61N 1/056 607/127 |
| 9,486,126 | B2 | 11/2016 | West et al. | |
| 2004/0010245 | A1 | 1/2004 | Cerier et al. | |
| 2004/0102830 | A1 * | 5/2004 | Williams | A61N 1/0573 607/125 |
| 2004/0153098 | A1 * | 8/2004 | Chin | A61B 17/3421 600/374 |
| 2004/0254572 | A1 * | 12/2004 | McIntyre | A61B 18/1477 606/41 |
| 2007/0142849 | A1 * | 6/2007 | Ewers | A61B 17/30 606/153 |
| 2012/0271327 | A1 | 10/2012 | West et al. | |
| 2013/0006287 | A1 | 1/2013 | West et al. | |
| 2017/0239448 | A1 * | 8/2017 | Cao | A61B 10/04 |
| 2018/0133464 | A1 * | 5/2018 | Taeubert | A61N 1/057 |
| 2018/0235604 | A1 | 8/2018 | Comee et al. | |
| 2019/0216601 | A1 | 7/2019 | Purcell et al. | |
| 2019/0328528 | A1 | 10/2019 | Purcell et al. | |
| 2020/0178956 | A1 * | 6/2020 | Mitelberg | A61B 17/0469 |

* cited by examiner

TISSUE ACQUISITION HELIX DEVICE

CROSS REFERENCE TO RELATED APPLICATIONS

The present application claims the benefit of and priority to U.S. Provisional Patent Application Ser. No. 62/930,700, filed on Nov. 5, 2019, titled TISSUE ACQUISITION HELIX DEVICE, the disclosure of which is incorporated herein by reference.

TECHNICAL FIELD

The disclosure is directed to devices for suturing tissue and more particularly to devices that work with an endoscope or similar device for endoscopically suturing tissue.

BACKGROUND

A variety of endoscopic treatments may result in defects (or wounds) that are too large for hemostasis clips to easily bridge and thus help to close the defect. Examples of such endoscopic treatments include removal of large lesions, tunneling under the mucosal layer, full thickness removal of tissue, treating other organs by passing outside of the gastrointestinal tract, and repair of post-surgical issues such as post-surgical leaks, failing surgical staple lines and anastomotic leaks. Endoscopic treatments also include bariatric revision procedures. Of the known devices and methods for endoscopically closing large defects, each has advantages and disadvantages.

SUMMARY

The disclosure is directed to several alternative designs, materials and methods of devices for endoscopically closing large defects. In an example, a tissue grasping device for use with an endoscope comprises a sheath defining a sheath lumen, a control wire slidably disposed within the sheath lumen, a tubular connector attached to a distal portion of the control wire, and a helical coil disposed over and attached to the tubular connector such that the tubular connector is between an outer surface of the control wire and an inner surface of the helical coil, the helical coil including a proximal region in which adjacent windings are in contact, and a distal region in which adjacent windings are spaced apart, the helical coil having a sharpened distal tip.

Alternatively or additionally to any of the above examples, the tubular connector is fixed against axial movement relative to the control wire.

Alternatively or additionally to any of the above examples, the tissue grasping device further comprising an inner sheath slidably disposed within the sheath lumen, the inner sheath having a lumen configured to receive the control wire.

Alternatively or additionally to any of the above examples, the inner sheath has a star-shaped transverse cross-section.

Alternatively or additionally to any of the above examples, the inner sheath is not attached to the helical coil.

Alternatively or additionally to any of the above examples, the control wire includes a visual indicator configured to indicate rotational movement of the control wire.

Alternatively or additionally to any of the above examples, the sheath lumen includes a proximal portion with a first inner diameter and a distal portion with a second inner diameter that is greater than the first diameter, wherein the helical coil is disposed within the distal portion of the sheath lumen.

Alternatively or additionally to any of the above examples, an outer diameter of the helical coil is greater than the inner diameter of the proximal portion Alternatively or additionally to any of the above examples, the control wire is devoid of any structure fixed to the proximal end of the helical coil.

Alternatively or additionally to any of the above examples, the tissue grasping device further comprising a heat-shrink tube disposed over at least a portion of the proximal region of the helical coil and at least a portion of the control wire adjacent the helical coil.

In another example, a tissue grasping device for use with an endoscope comprises a sheath defining a sheath lumen, a control wire slidably disposed within the sheath lumen, a helical coil disposed over and attached to a distal portion of the control wire, the helical coil including a proximal region in which adjacent windings are in contact, and a distal region in which adjacent windings are spaced apart, the helical coil having a sharpened distal tip, and wherein the control wire is devoid of any structure fixed to the proximal end of the helical coil.

Alternatively or additionally to any of the above examples, the helical coil is attached to the control wire with adhesive.

Alternatively or additionally to any of the above examples, the proximal region of the helical coil includes a first zone in which the adjacent windings are in contact, and a second zone proximal of the first zone, wherein adjacent windings in the second zone are spaced apart.

Alternatively or additionally to any of the above examples, the tissue grasping device further comprising a connection element disposed within the second zone, the connection element configured to connect the helical coil to the control wire.

Alternatively or additionally to any of the above examples, the connection element is a weld.

Alternatively or additionally to any of the above examples, the control wire includes a visual indicator configured to indicate rotational movement of the control wire.

Alternatively or additionally to any of the above examples, the sheath lumen includes a proximal portion with a first inner diameter and a distal portion with a second inner diameter that is greater than the first diameter, wherein the helical coil is disposed within the distal portion of the sheath lumen.

Alternatively or additionally to any of the above examples, an outer diameter of the helical coil is greater than the inner diameter of the proximal region.

Alternatively or additionally to any of the above examples, the proximal region has a close fit over the control wire.

In a further example, a tissue grasping device for use with an endoscope comprises an outer sheath defining a sheath lumen, a control wire slidably disposed within the sheath lumen, an inner sheath slidably disposed within the sheath lumen, the inner sheath having a lumen configured to receive the control wire, a tubular connector attached to a distal portion of the control wire, and a helical coil disposed over and attached to the tubular connector such that the tubular connector is between an outer surface of the control wire and an inner surface of the helical coil, the helical coil including a proximal region in which adjacent windings are in contact, and a distal region in which adjacent windings are spaced apart, the helical coil having a sharpened distal tip, wherein the tissue grasping device is devoid of any structures fixed to the proximal end of the helical coil.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE FIGURES

The disclosure may be more completely understood in consideration of the following description of in connection with the accompanying drawings, in which.

Figure 1:
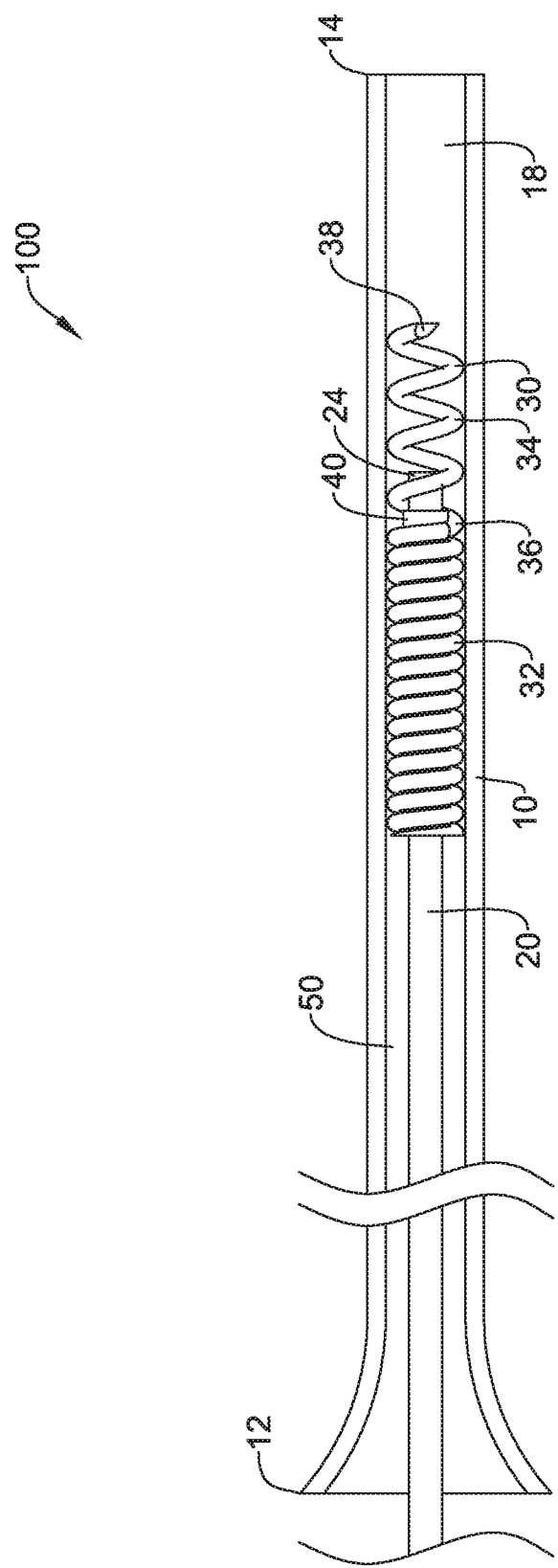
FIG. 1 is a side partial cut-away view of an illustrative tissue grasping device in accordance with an example of the disclosure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

The disclosure pertains to devices that are configured to be used in combination with an endoscope or a similar delivery device for closing wounds within the body. In some instances, tissue grasping devices described herein may be configured such that they may be used within a single working or available channel of an endoscope, and in some cases may be operated by a single individual, although in some cases a second individual may be involved. In some cases, the tissue grasping devices described herein may be considered as operating along a single line of operation. The device itself may be translatable distally and proximally within a working channel, and a handle portion may itself be translatable distally and proximally along the same line of operation in advancing and retracting the tissue grasping device. The device may be configured to enable the tissue to be held in a suitable position for suturing.

The tissue grasping device described herein may be used with a suture device such as that described in U.S. Patent Publication No. 2018/0235604, published on Aug. 23, 2018, the entire contents of which are incorporated herein by reference. Additionally, the tissue grasping device may be used outside of the suturing system for any applications that require tissue grasping and/or acquisition.

FIG. 1 shows an example tissue grasping device 100 that may be considered as being configured for use in combination with a delivery system including a lumen that extends through the delivery system. For example, the delivery system may be an endoscope having a working channel. The delivery system may also be a catheter. The tissue grasping device 100 may be configured to grasp tissue for suturing through the endoscope. It is understood that the tissue grasping device may stabilize a selected portion of tissue for suturing. The tissue grasping device 100 may include a sheath 10 having a proximal end 12, a distal end 14, and a sheath lumen 18 extending therebetween. The sheath 10 may be a flexible tube sized and configured for insertion through an endoscope. In some examples, the proximal end 12 of the sheath may be flared, as shown in FIG. 1, for joining to a handle. The distal end 14 including the lumen 18 may also be flared (not shown). In other examples, the proximal end 12 may be cylindrical. A control wire 20 may be slidable disposed within the sheath lumen 18. The control wire 20 may be an elongate flexible resilient wire, a flexible torque transmitting multi-filament cable, a laser cut hypotube, or a catheter. The control wire 20 may be a solid structure. In other examples, the control wire 20 may have a lumen. The control wire 20 is freely slidable longitudinally and rotatable within the sheath 10. The control wire 20 may be nitinol, stainless steel, or other metal that provides the desired flexibility. Nitinol allows for flexibility without kinking.

A helical coil 30 having a plurality of windings may be disposed over and attached to a distal portion of the control wire 20, as shown in FIG. 1. The helical coil 30 may be attached to the control wire 20 by welding, adhesive, or other connection means to provide a permanent connection. The helical coil 30 may include a proximal region 32, a distal region 34, and an intermediate region 36 therebetween. In the proximal region 32 adjacent windings may be in contact with one another, while in the distal region 34 the adjacent windings may be spaced apart. The windings being in contact with one another in the proximal region 32 of the coil may provide rigidity that prevents the helical coil 30 from bending when under perpendicular loads. The windings in the intermediate region 36 may have a non-constant pitch resulting in gradually increasing spacing, transitioning from the adjacent windings being in contact with one another in the proximal region 32 to the spaced apart windings in the distal region 34. The distal end 24 of the control wire 20 may extend into distal region 34 of helical coil 30, preventing tissue being caught in the area of small spaces between windings in the intermediate region 36. The helical coil 30 may have a sharpened distal tip 38. The helical coil 30 may be a solid round metal wire, and may be formed to have a diameter greater than a diameter of the control wire. The helix shape provides generally superior tissue grasping capability when used with a closure system. The closure device requires tissue to be grasped and then pulled into a suturing window. The sharpened distal tip 38 of the helical coil 30 is easy to rotate into tissue by rotating the control wire 20 in a first direction, and holds on to the tissue well when pulled. In some examples, the distal region 34 of the helical coil 30 may include one to ten, or three to five full helical turns, which may aid in securing tissue for suturing. The helical coil 30 may also be advantageous for acquiring tissue in the presence of fluids versus standard forceps-type graspers which have the tendency to slip in those conditions, particularly in the stomach. After suturing, the helical coil 30 is removed from the tissue by reversing the rotation of the control wire 20.

Figure 2:
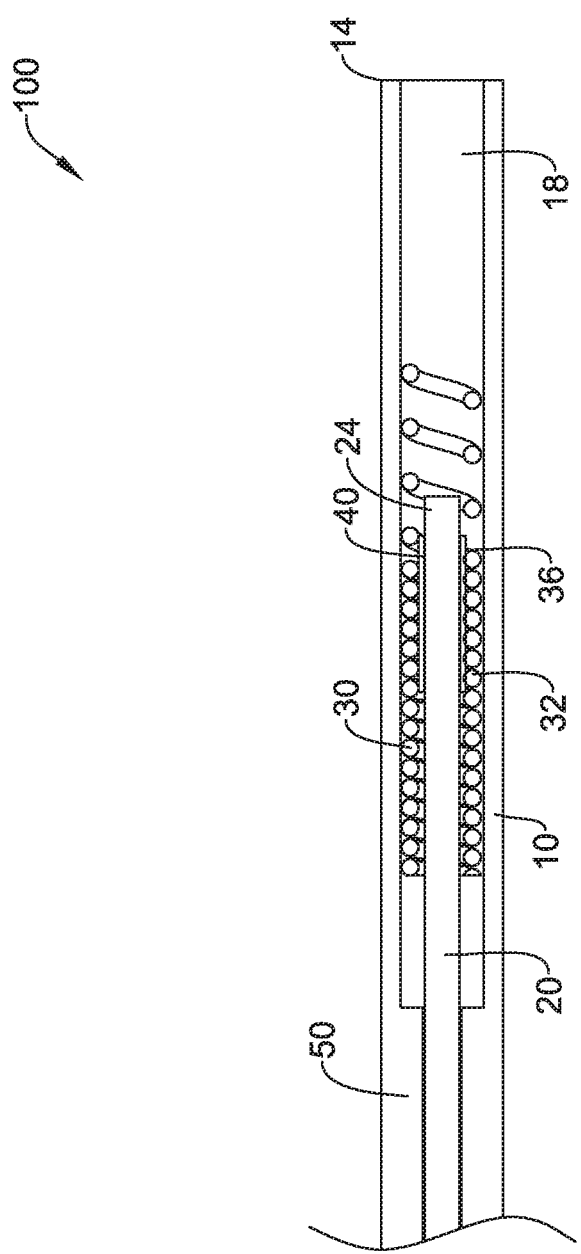
FIG. 2 is a cross-sectional view of the distal portion of the illustrative tissue grasping device of FIG. 1.

In some examples, the tissue grasping device 100 may include a tubular connector 40 attached to a distal portion of the control wire 20, just proximal of the distal end 24. The tubular connector 40 may be fixed against axial movement relative to the control wire 20. In some examples, the tubular connector 40 may be soldered or welded onto the control wire 20, or attached with adhesive. In other examples, the tubular connector 40 may be crimped onto the control wire 20. The helical coil 30 may be disposed over and attached to the tubular connector 40 such that the tubular connector 40 is between an outer surface of the control wire 20 and an inner surface of the helical coil 30. The tubular connector 40 may have a length such that it extends only under portions of the proximal region 32 and intermediate region 36 of the helical coil 30, as shown in FIG. 2. The tubular connector 40 may be an elongate hollow tube, and may be solid, on include slots, slits, recesses or the like. In some examples the helical coil 30 may be attached to the control wire 20 only via the tubular connector 40. In other examples, the helical coil 30 may be attached to the tubular connector 40 and also attached directly to the control wire 20. In some examples, the control wire 20 may be devoid of any structures fixed to the control wire 20 proximal of the helical coil 30. In particular, the control wire 20 may be devoid of any structure attached to the proximal end of the helical coil 30. In such an example, the helical coil 30 is attached to the distal end of the control wire 20 in the absence of any structure such as a tubular element, sleeve, support, or additional member disposed at the distal end region of the control wire 20 at the proximal end of the helical coil 30.

In some examples, the tissue grasping device 100 may include an inner sheath 50 slidably disposed within the sheath lumen 18 and over the control wire 20. The inner sheath 50 may have a lumen configured to receive the control wire 20 in a close fit such that the control wire 20 is freely longitudinally slidable and rotatable within the inner sheath 50 with minimal radial movement while maintaining the control wire 20 within the center of the sheath 10 and preventing the control wire 20 from kinking. The inner sheath 50 may have a length less than the distance between the proximal region 32 of the helical coil 30 and the proximal end 12 of the sheath 10. The inner sheath 50 is not attached to the helical coil 30. The inner sheath 50 may be a cylindrical tube with an outer diameter providing a close fit with the inner surface of the sheath lumen 18. In other examples, the inner sheath 50 may be formed with the sheath 10 as a single monolithic element, as described below with reference to FIG. 7.

Figure 3:
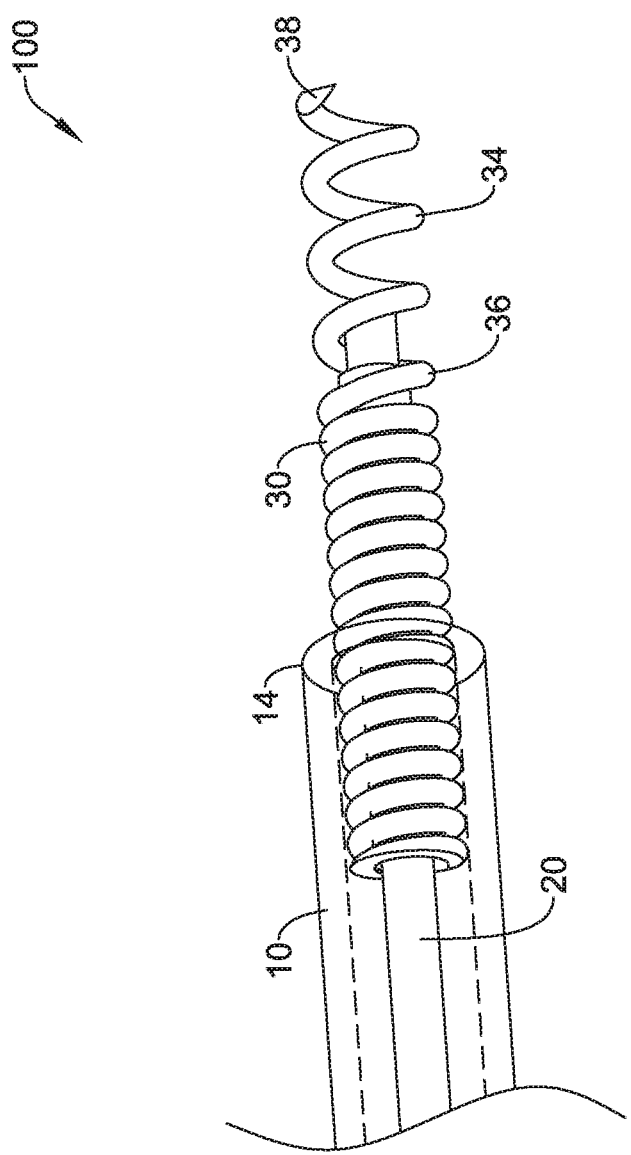
FIG. 3 is a perspective view of the illustrative tissue grasping device of FIG. 1, shown in an extended position.

The control wire 20 may be both longitudinally and rotationally movable within the sheath 10. As shown in FIG. 3, pushing the control wire 20 longitudinally moves at least a portion of the helical coil 30 out of the distal end 14 of the sheath 10. With at least the distal region 34 of the helical coil 30 positioned distal of the distal end 14 of the sheath 10 and in contact with tissue, rotation of the control wire 20 in a first direction causes the sharpened distal tip 38 of the helical coil to pierce the tissue. When the helical coil 30 is positioned substantially perpendicular to the tissue, continued rotation of the helical coil 30 in the first direction may cause the sharpened distal tip 38 to be driven deeper into the tissue, in a corkscrew manner. If the helical coil 30 is positioned tangential to the tissue, then continued rotation in the first direction may cause the sharpened distal tip 38 to repeatedly enter and exit the tissue, which may temporarily hold two adjacent edges of tissue together. Either position may hold the tissue and allow a suture device to suture the tissues together. The control wire 20 may then be rotated in the opposite direction to withdraw the helical coil 30 from the tissue. The presence of the control wire 20 through the intermediate region 36 may prevent tissue from becoming trapped between the closely spaced windings.

Figure 4:
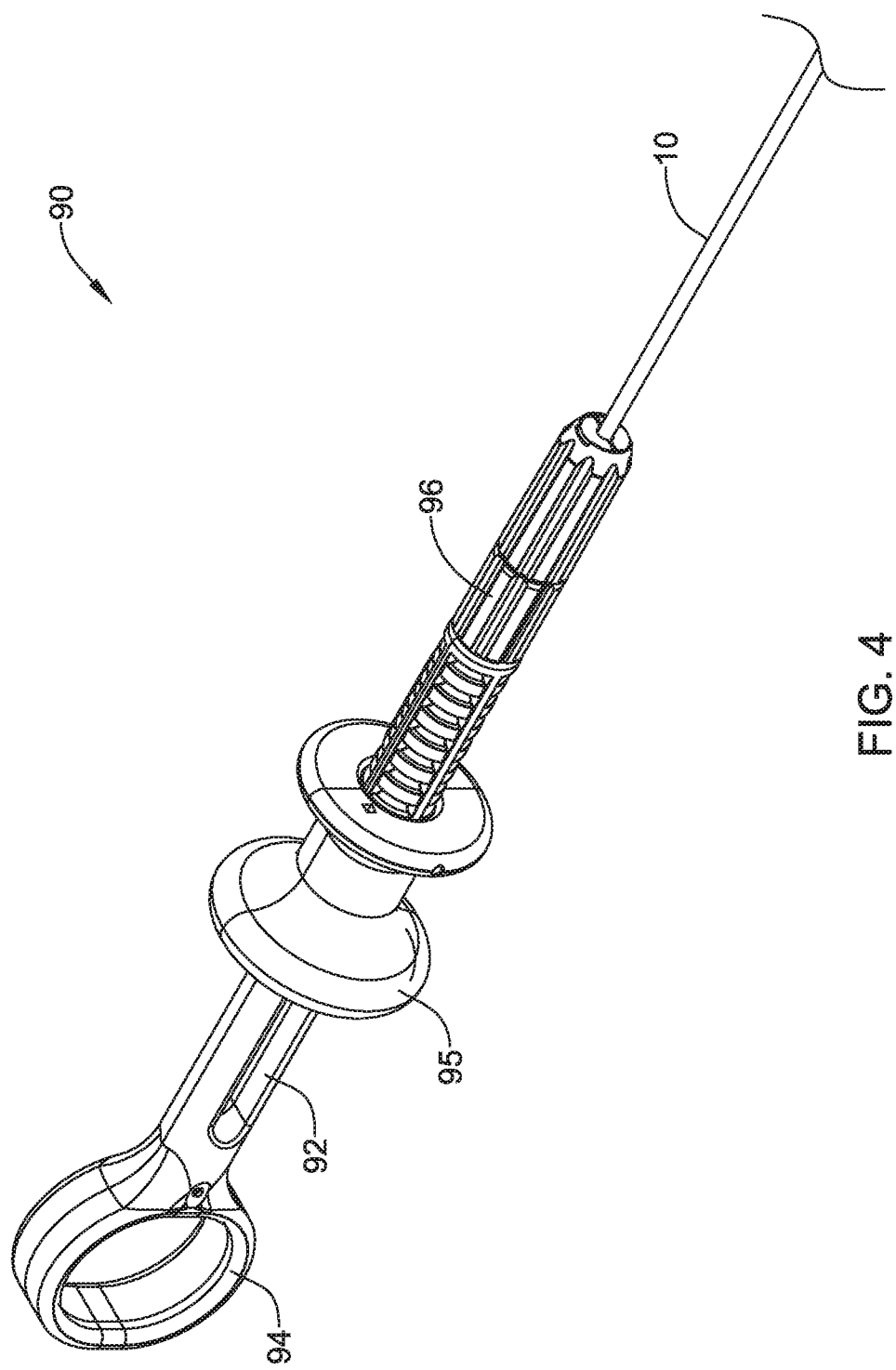
FIG. 4 is a perspective view of a handle assembly for use with the illustrative tissue grasping device of FIG. 1.

FIG. 4 shows an example of a user interface handle 90 for actuating the tissue grasping device 100 to move the control wire 20 longitudinally and rotationally. The handle 90 may include a handle portion 92 with a proximal finger loop 94 and a translating handle 95 connected to the control wire 20.

The translating handle 95 is slidable along the handle portion 92 to advance and retract the helical coil 30 from the sheath 10. As shown in FIG. 4, the translating handle 95 is in the forward position, indicating the helical coil 30 is in the extended position as shown in FIG. 3. Sliding the translating handle 95 towards the finger loop 94 may move the helical coil 30 proximally into the sheath 10, as shown in FIG. 1. Retracting the helical coil 30 into the sheath 10 when advancing down a working channel protects the sharpened distal tip 38 from damage and surrounding tissue from the sharp tip. The handle 90 may also include a rotatable control knob 96 that is directly connected to the control wire 20. Rotating the control knob 96 rotates the control wire 20 and the helical coil 30 at the distal end of the device.

Figure 5:
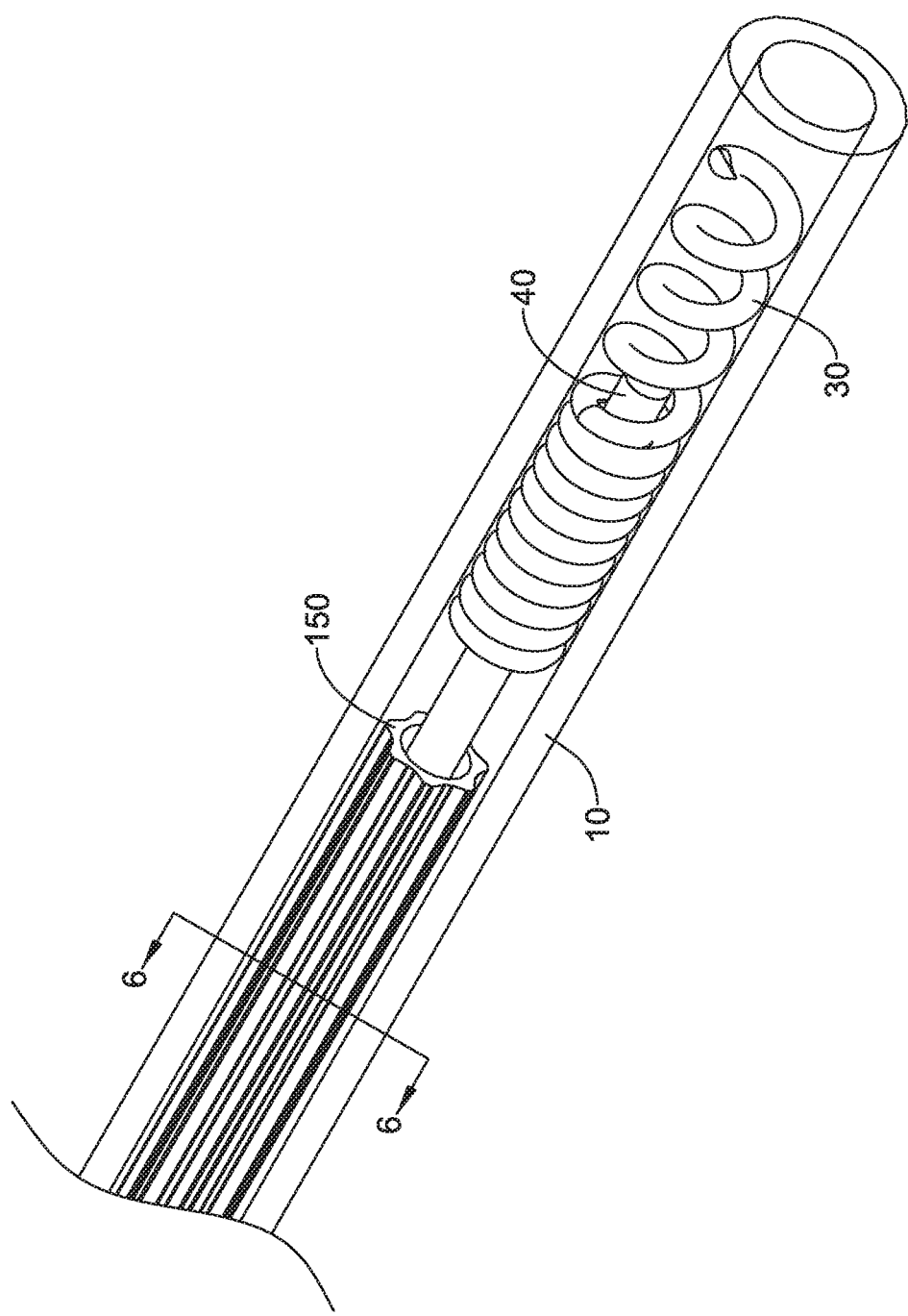
FIG. 5 is a perspective view of a portion of an illustrative tissue grasping device in accordance with another example of the disclosure.
Figure 6:
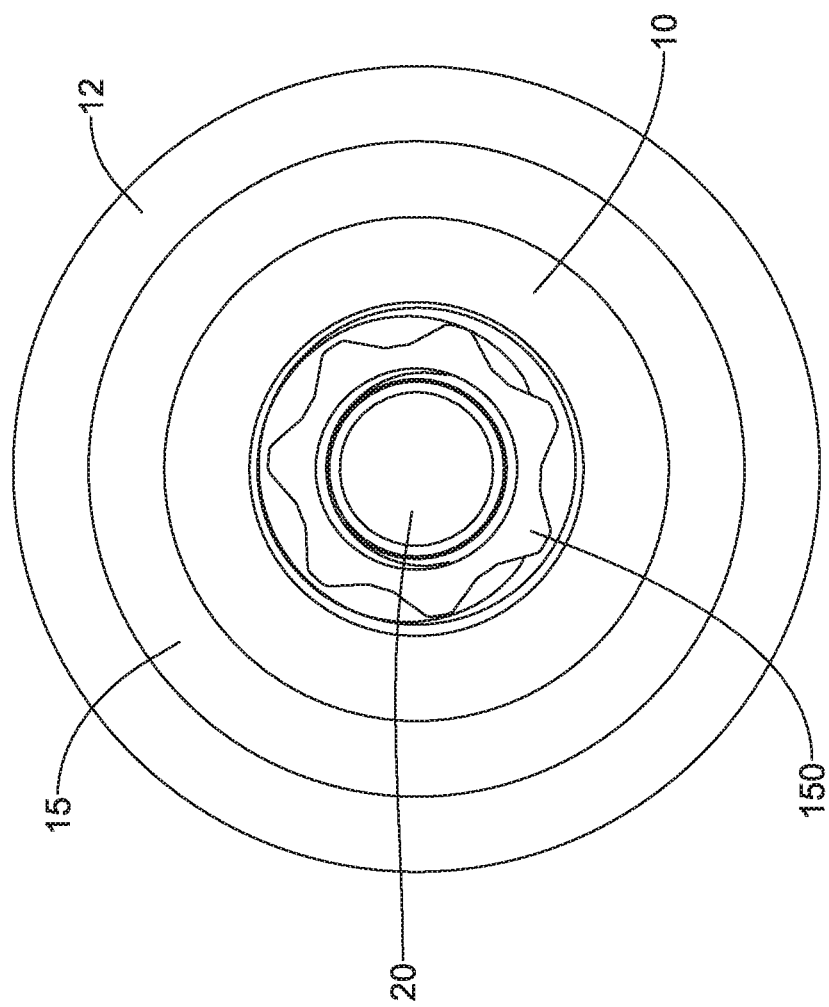
FIG. 6 is a cross-sectional view of the illustrative tissue grasping device of FIG. 5, taken along line 6-6.

In some examples, the inner sheath may have a non-circular transverse cross-section. For example, the inner sheath 150 may have a star-shaped transverse cross-section, as shown in FIGS. 5-6. The star-shaped inner sheath 150 may reduce friction against the inner surface of the sheath 10, improving slidability. In other examples, the outer and/or inner surface of the inner sheath 150 may include a lubricious coating. The cross-section shown in FIG. 6 illustrates the flared region 15 on the proximal end 12 of the sheath 10.

Figure 7:
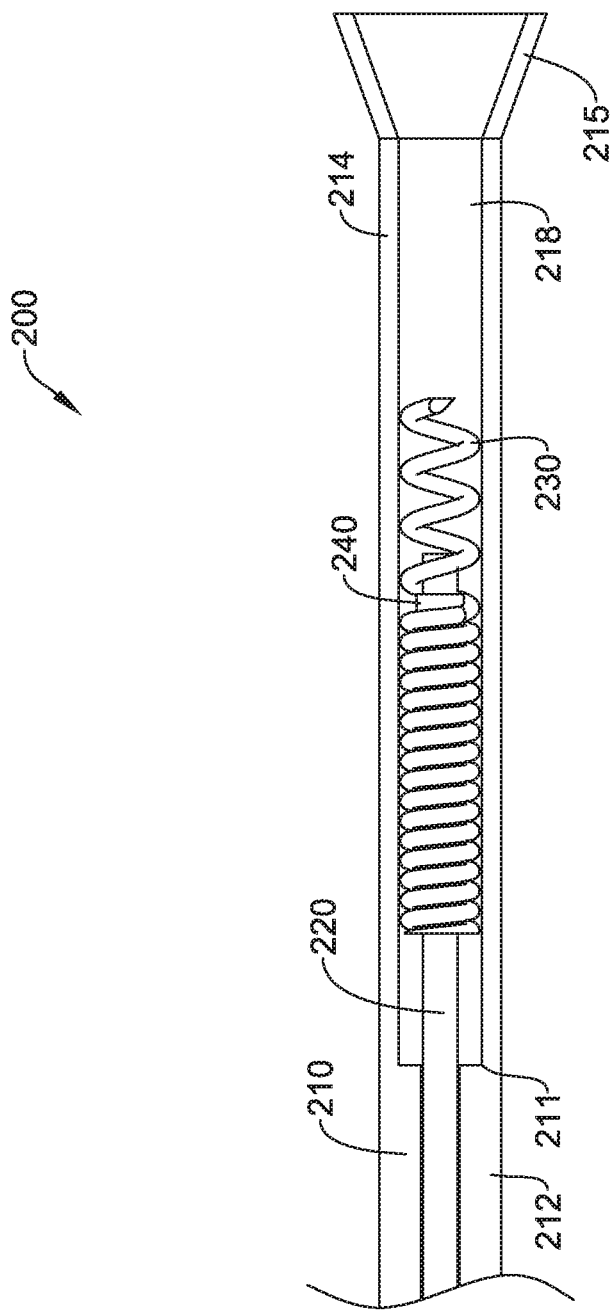
FIG. 7 is a side partial cut-away view of a portion of an illustrative tissue grasping device in accordance with another example of the disclosure.

In another example, the tissue grasping device 200 may have an inner and outer sheath defined by a single monolithic piece. As shown in FIG. 7, the sheath 210 may include a proximal portion 212 and a distal portion 214, with the inner diameter of the distal portion 214 being larger than the inner diameter of the proximal portion 212. The sheath 210 may include a step 211 from the inner diameter of the proximal portion 212 up to the larger inner diameter of the distal portion 214, as shown in FIG. 7. This step may be a gradual even ramp or an abrupt step 211. The tissue grasping device 200 shown in FIG. 7 has an abrupt step 211. The proximal portion 212 of the sheath 210 may have an inner diameter forming a close fit around the control wire 220, which may provide for a smooth actuation and rotation of the control wire 220. The helical coil is disposed within the distal portion 214. In some examples, the distal portion 214 may include a flared distal end 215, including an enlarged lumen 218 as shown in FIG. 7, which may aid in re-inserting the coil 230 proximally into the sheath 210 after the coil 230 has been extended distally completely out of the sheath 210. It will be understood that the flared distal end may be incorporated into any of the devices described herein.

Figure 8:
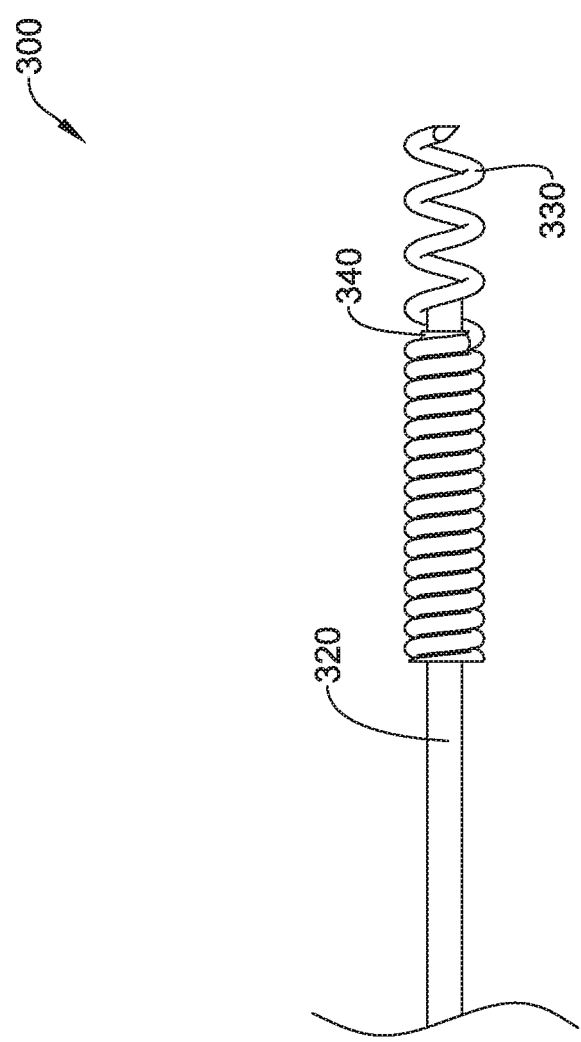
FIG. 8 is a side view of a portion of an illustrative tissue grasping device in accordance with another example of the disclosure.

A further example of tissue grasping device 300 includes no inner sheath, stepped extrusion, or outer sheath, as shown in FIG. 8. This device consists of only the control wire 320, tubular connector 40, and helical coil 30, but is devoid of any sheath, with the control wire 320 and helical coil 30 always exposed. The tissue grasping device 300 would pass down the working channel of the endoscope and would be actuated by advancing the helical coil out 330 of the working channel. The working channel acts as the outer sheath.

Figure 9:
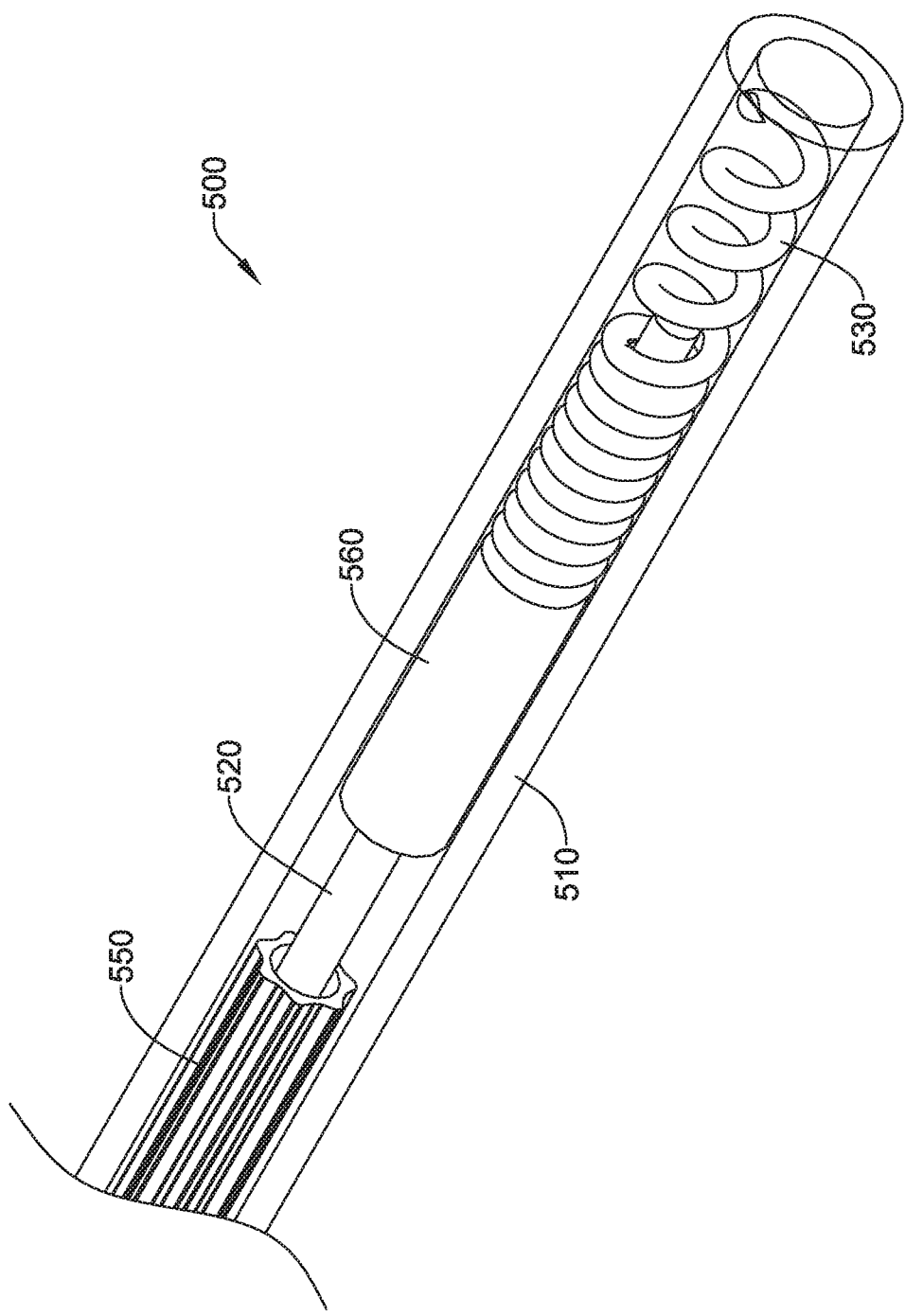
FIG. 9 is a perspective view of a portion of an illustrative tissue grasping device in accordance with another example of the disclosure.
Figure 10:
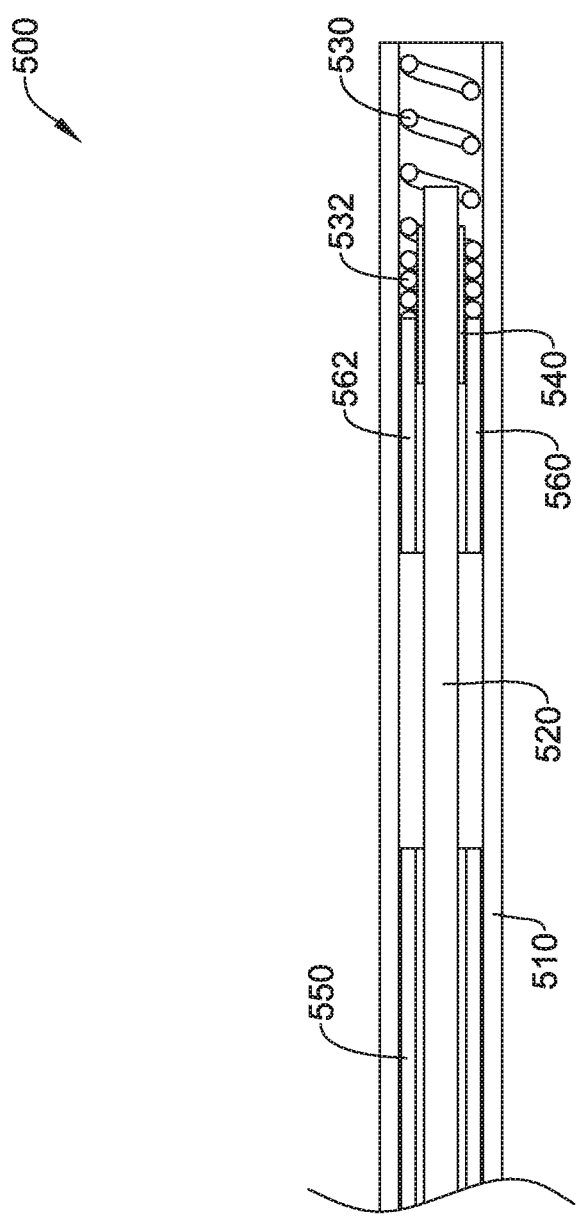
FIG. 10 is a cross-sectional view of the illustrative tissue grasping device of FIG. 9.

In the example shown in FIGS. 9 and 10, the tissue grasping device 500 may include an outer cannula 560 fixed to the proximal end of the helical coil 530. The outer cannula 560 may extend proximal of the proximal region 532 and may be fixed to the control wire 520 with a connector 562. The connector 562 may be adhesive such as an epoxy, or a weld, solder, or separate tubular connector. The tubular connector 540 may extend proximal of the helical coil 530 such that it extends into the lumen of the outer cannula 560, as shown in FIG. 10. The outer cannula 560 may be attached to the tubular connector 40 with adhesive, solder, or a weld. The combination of outer cannula 560 and tubular connector 40 may provide additional support to the helical coil 530 when in the extended position.

Figure 11:
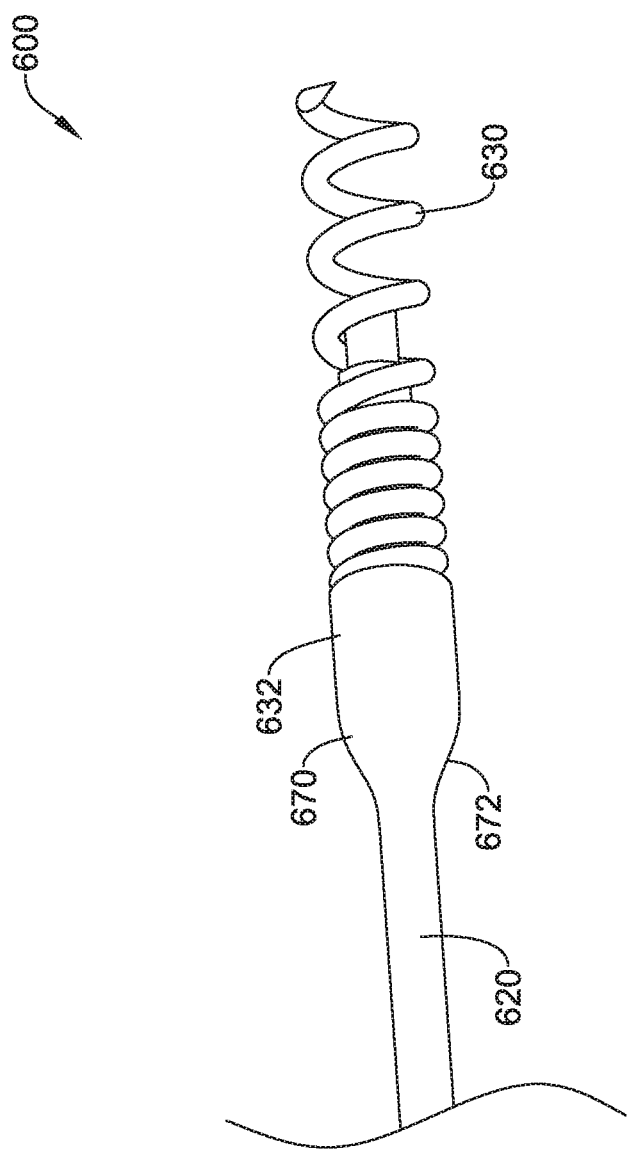
FIG. 11 is a perspective view of a portion of an illustrative tissue grasping device in accordance with another example of the disclosure.
Figure 12:
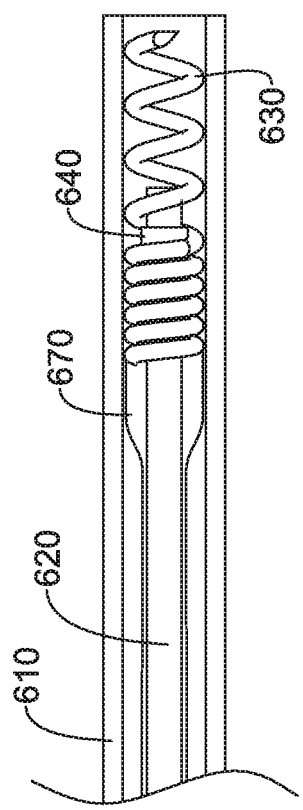
FIG. 12 is a cross-sectional view of the illustrative tissue grasping device of FIG. 11.

In the above examples, the transition between the proximal end of the helical coil and the control wire may be a sharp step. In other examples, the tissue grasping device 600 may have a smoother transition provided by disposing a heat-shrink tube or wrap 670 over at least the proximal region 632 of the helical coil 630, a portion of the tubular connector 640 extending proximally of the helical coil 630, and the portion of the control wire 620 adjacent the proximal end of the helical coil 630, as shown in FIGS. 11 and 12. The heat-shrink wrap 670 may provide a smooth gradual transition ramp 672 between the outer diameters of the helical coil 630 and the control wire 620. If the helical coil 630 extends too far out of the catheter, the heat-shrink wrap 670 may act as a smooth transition ramp when retracting the helical coil 630 back into the sheath 610.

In some examples, the control wire 620 may also include markings or other visual indicator to assist with visualization of rotation. As shown in FIG. 11, the control wire 620 has a visual indicator including a spiral striped pattern of two contrasting colors, which provides an indication of how much the control wire 620 is rotated and thus the degree of rotation of the helical coil 630. In some examples, the markings may include helical stripes of different colors extending at least along the proximal portion of the control wire 620. In other examples, the markings may be disposed along the entire length of the control wire 620. When the heat-shrink warp 670 is present, the markings may be disposed on the heat-shrink wrap 670.

Figure 13:
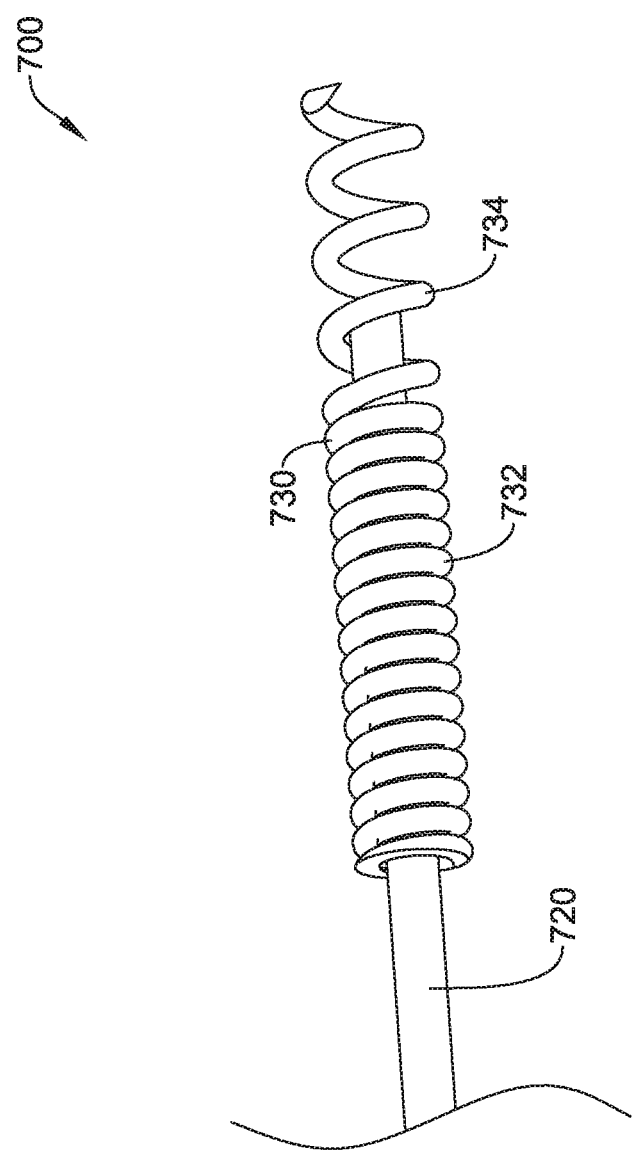
FIG. 13 is a side cross-sectional view of a portion of an illustrative tissue grasping device in accordance with another example of the disclosure.

In some examples of a tissue grasping device 700, the tubular connector 40 may be eliminated, with the helical coil 730 configured such that the constricting force the helical coil makes around the control wire 720 secures the helical coil 730 to the control wire 720, as shown in FIG. 13. In this example, the tissue grasping device 700 consists only of the control wire 720 and the attached helical coil 730. The helical coil 730 may have a structure similar to the helical coil 30 shown in FIG. 1, including a proximal region 732 in which adjacent windings touch one another, and a distal region 734 in which adjacent windings are spaced apart. The control wire 720 may have features on it to help engage the helical coil 730. For example, the control wire 720 may include one or more groove or ridge (not shown) configured to receive the windings of the control wire 720. In some examples, solder or adhesive may be added to secure the helical coil 730. Alternatively, direct welding may be used to secure the helical coil 730 to the control wire 720 if the materials allow. In some examples, the tissue grasping device 700 may include the sheath 10 and/or the inner sheath 50 discussed above.

Figure 14:
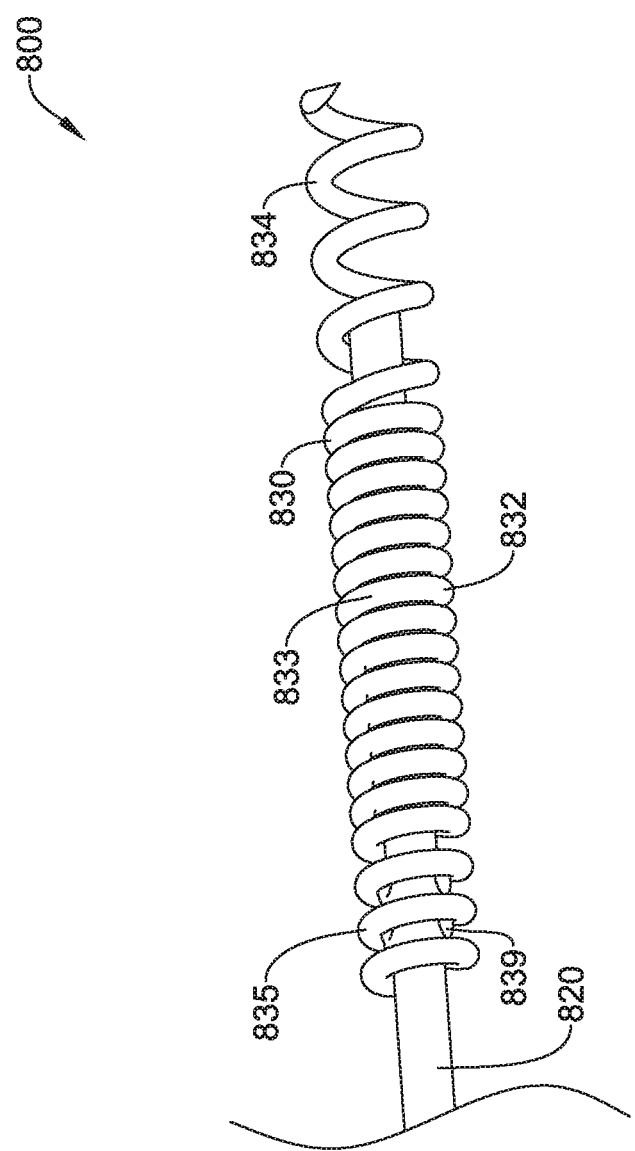
FIG. 14 is a side view of a portion of an illustrative tissue grasping device in accordance with another example of the disclosure.

In order to provide increased bonding surface area for the soldered or adhesive connection, the proximal region 832 of the helical coil 830 may be separated into a first zone 833 and a second zone 835 disposed proximal of the first zone 833, as shown in FIG. 14. The windings in the first zone 833 may remain in contact with one another while the windings in the second zone 835 may be separated, similar to the spaced-apart windings in the distal region 834. A connection element such as solder or adhesive 839 may be applied to the second zone 835, as shown in FIG. 14.

FIGS. 15 through 19 provide an illustrative but non-limiting example of a distal assembly 14c being used to perform a tissue repair using a tangential approach. A tangential approach may be used, for example, when repairing a larger wound that requires suturing through thicker or more tissue. Bariatric revision procedures are an example of a procedure that would benefit from a tangential approach. The distal assembly 14c and associated suture translation assemblies are described in U.S. Patent Publication No. 2018/0235604, the entire contents of which are incorporated herein by reference. It will be appreciated that the distal assembly 14c, in performing the illustrated procedure, may be secured to the distal end of an endoscope or other delivery device, and may be used in combination with any suture translation assembly described in the above patent publication.

Figure 15:
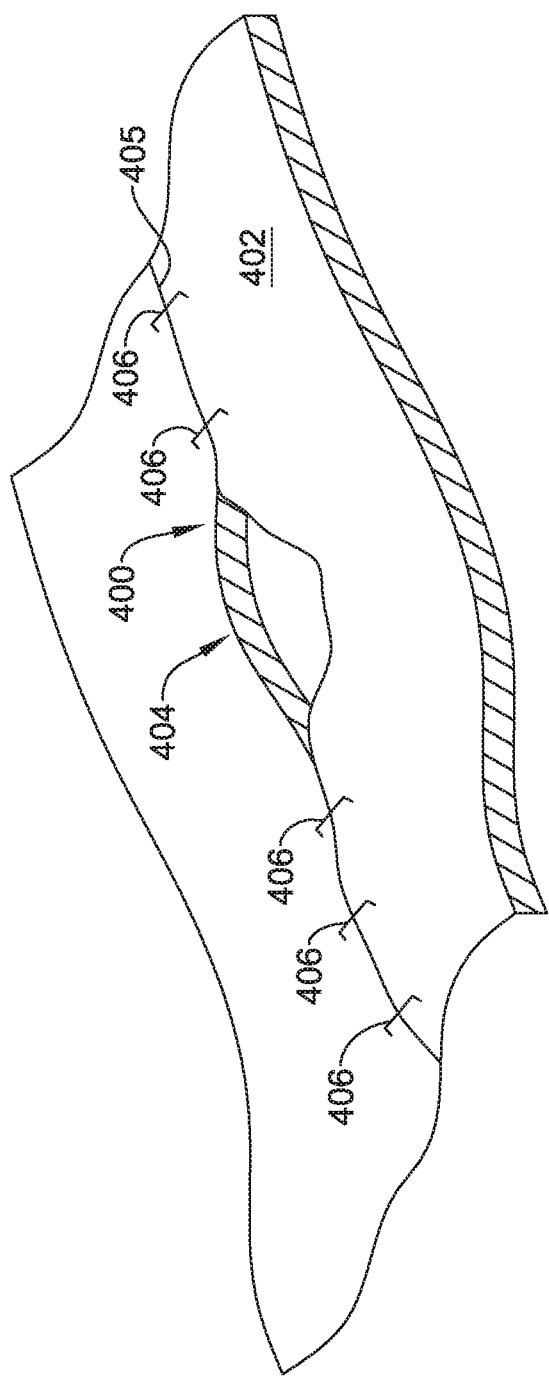
FIGS. 15 through 19 illustrate use of a tissue grasping device with a suture device in a tangential approach that may be used in suturing thicker tissue and/or larger wounds such as those encountered during a bariatric revision procedure in accordance with an example of the disclosure.

FIG. 15 shows a defect 400 within tissue 402. In some cases, the defect 400 may include a remaining open portion 404 along a staple or suture line 405. In some instances, a portion of the defect 400 has already been closed using staples 406, and in some cases the remaining open portion 404 may be positioned such that stapling is either inappropriate or difficult to perform, and suturing is desired to close the defect 400.

Figure 16:
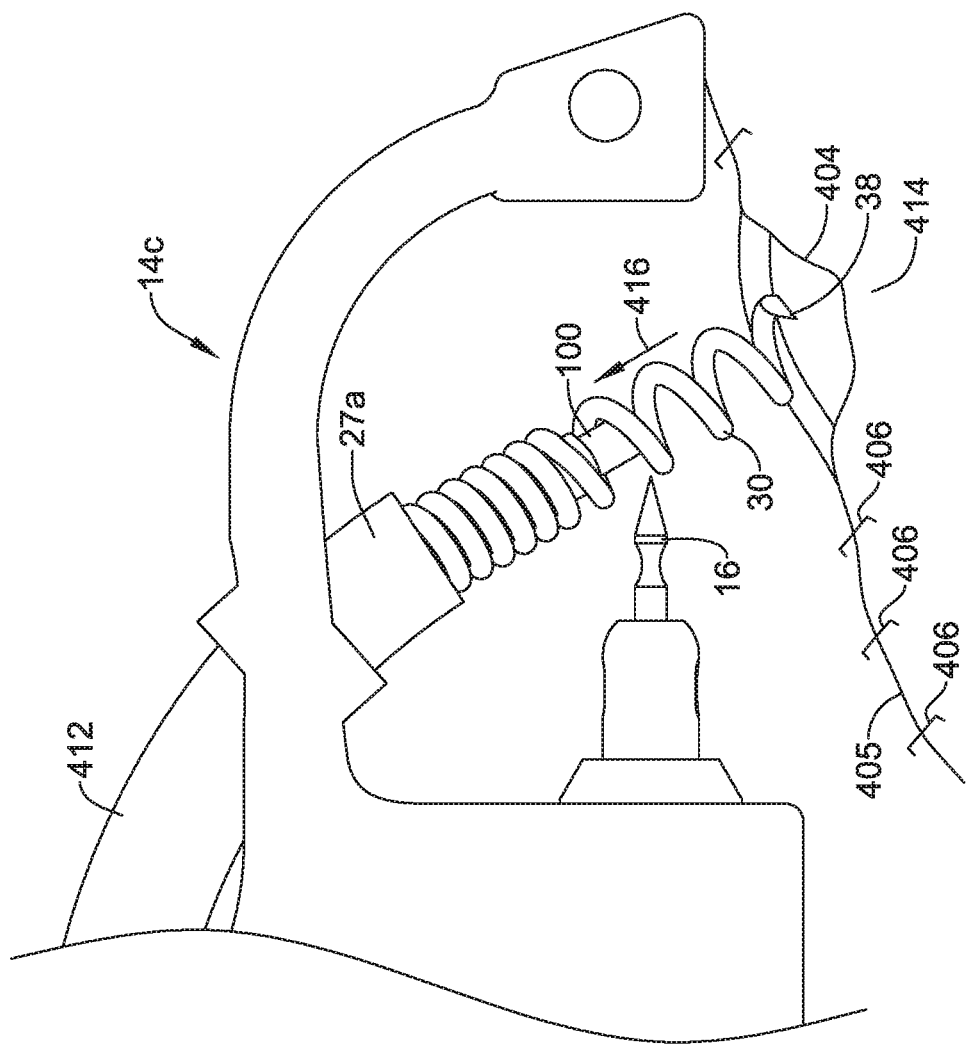
Figure 17:
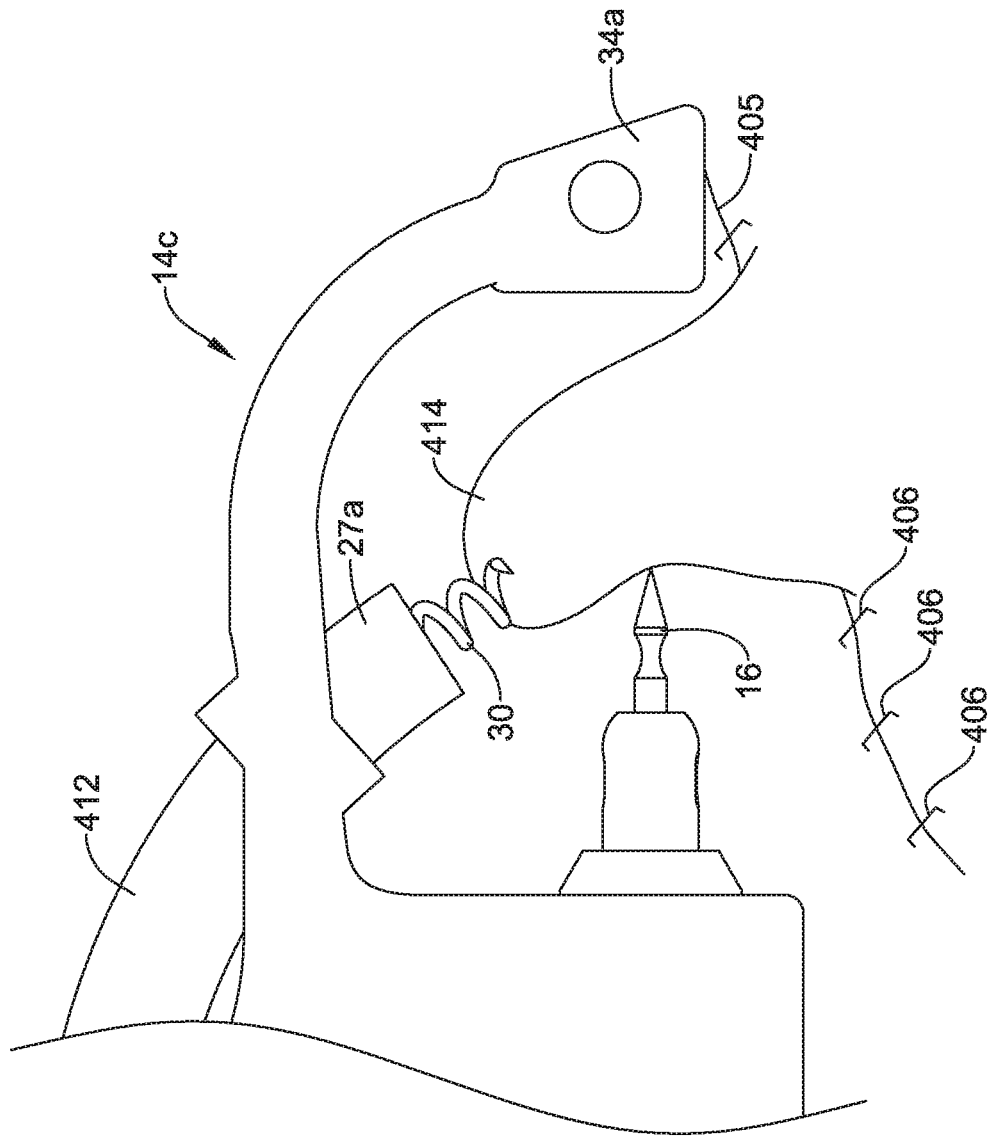
Figure 18:
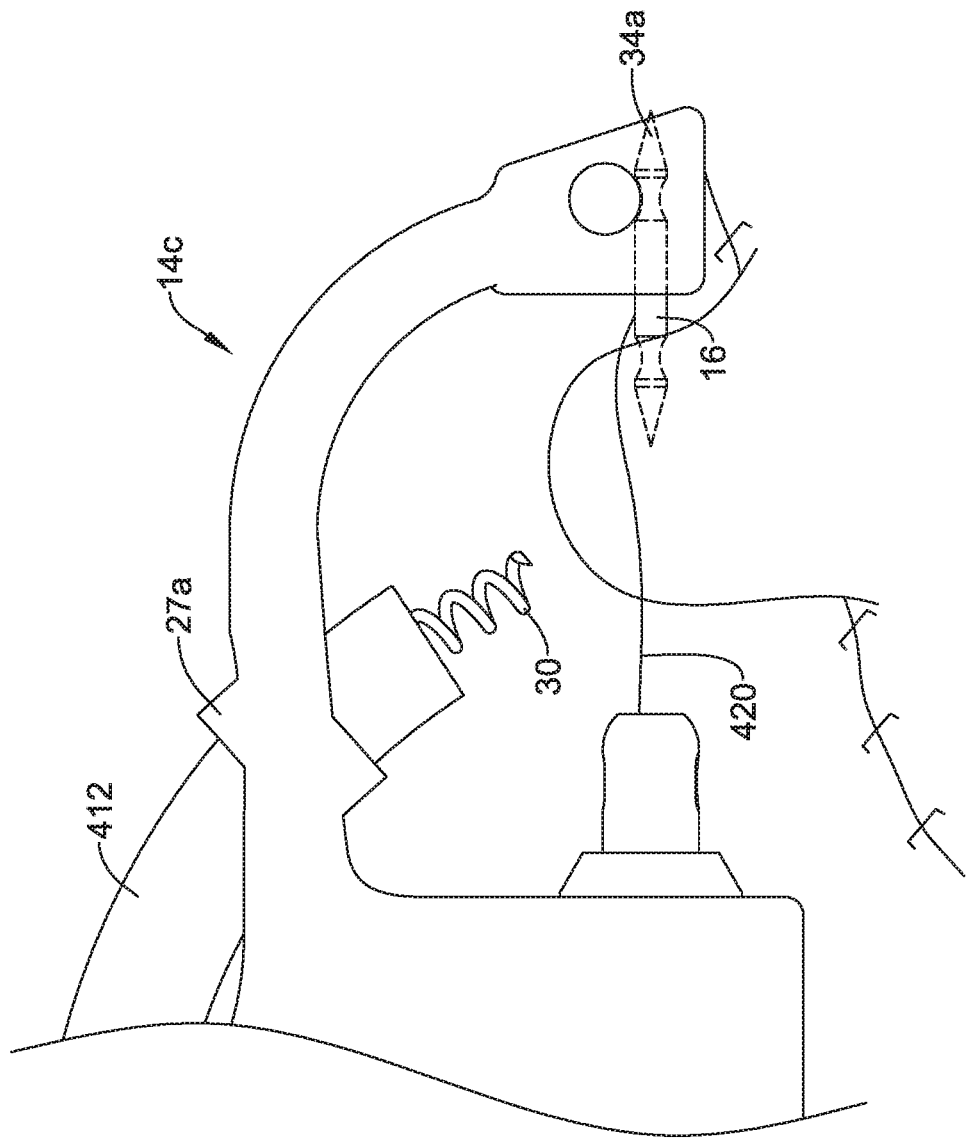
Figure 19:
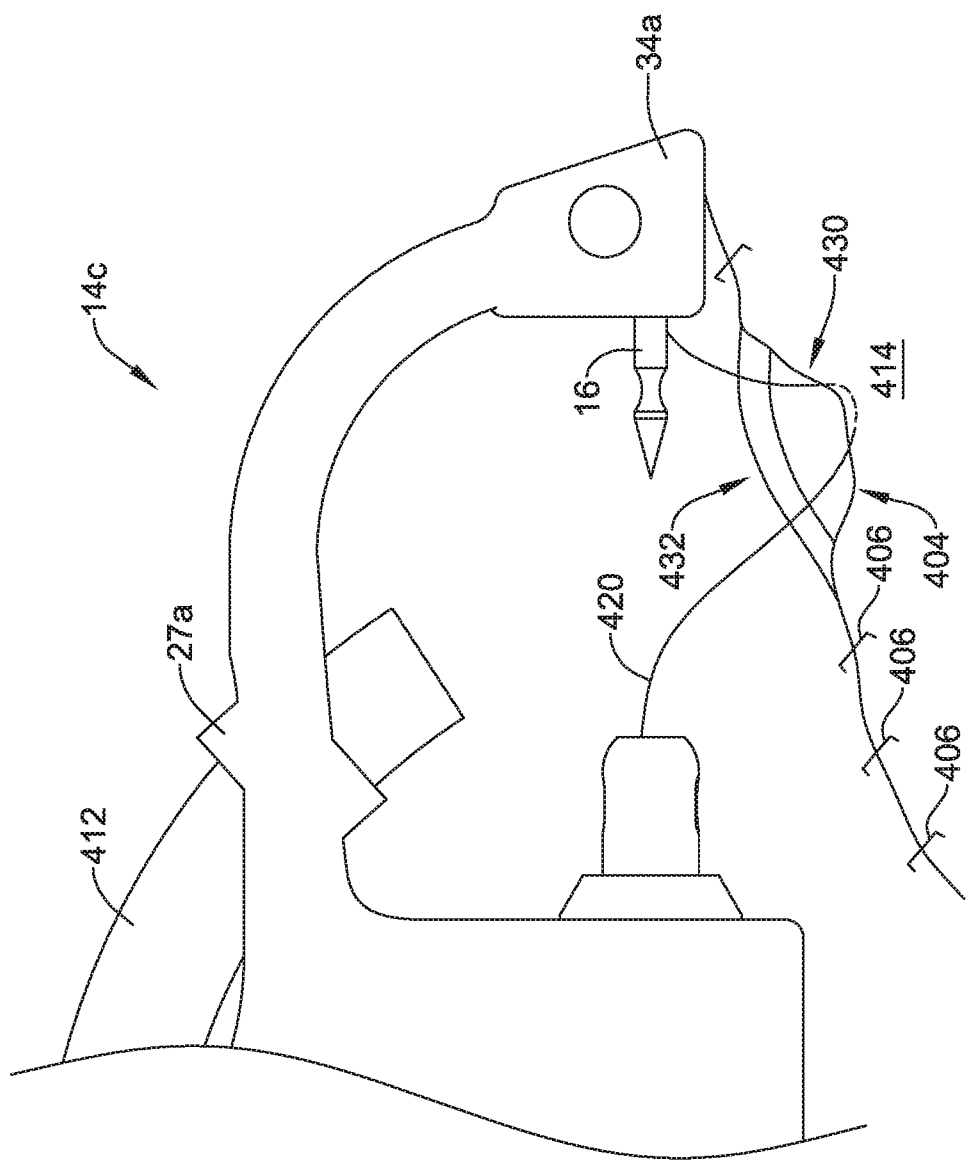

Starting in FIG. 16, the distal assembly 14c has been positioned relative to the defect 400. A tissue grasping device 100 extends through a tubular member 412 that is secured relative to the guide structure 27a, and may be positioned such that the sharpened distal tip 38 of the helical coil 30 may be rotated into tissue 414 proximate one side of the remaining open portion 404 of the defect 400. With the helical coil 30 embedded within the tissue 414, the tissue 414 may be pulled upward by retracting the tissue grasping device 100, as denoted by an arrow 416. As the tissue 414 is pulled upward, as noted in FIG. 17, suturing may begin. In FIG. 18, it can be seen that the helical coil 30 has been reversed out of the tissue and the needle 16 has been passed through the tissue 414 and has been grasped by the end cap 34a, thereby pulling a suture 420 through the tissue 414. As can be seen in FIG. 19, the suture 420 now extends through the tissue 414 on a first side 430 of the remaining open portion 404 of the defect 400. The suturing process may continue by repeating the aforementioned steps on the second side 432 of the remaining open portion 404 of the defect 400.

It will be appreciated that a variety of different materials may be used in forming the devices described herein. In some cases, a variety of different metals may be used. Illustrative but non-limiting examples of suitable metals include titanium, stainless steel, magnesium, cobalt chromium and others. In some embodiments, for example, the devices described herein may include any suitable polymeric material, including biocompatible materials such as polyurethane or silicone. Other suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A tissue grasping device for use through an endoscope, comprising:
   a sheath defining a sheath lumen;
   a control wire slidably disposed within the sheath lumen;
   a tubular connector fixed to a distal portion of the control wire; and
   a helical coil disposed over and fixed to the tubular connector such that the tubular connector is between an outer surface of the control wire and an inner surface of the helical coil, the helical coil including a proximal region in which adjacent windings are in contact, wherein the helical coil is slidable relative to the sheath from an undeployed configuration in which an entirety of the helical coil is disposed completely within the sheath to a deployed configuration in which at least a distal portion of the helical coil extends distally beyond a distal end of the sheath; and
   a distal region in which adjacent windings are spaced apart, the helical coil having a sharpened distal tip.

2. The tissue grasping device of claim 1, wherein the tubular connector is fixed against axial movement relative to the control wire.

3. The tissue grasping device of claim 1, further comprising an inner sheath slidably disposed within the sheath lumen, the inner sheath having a lumen configured to receive the control wire, the inner sheath having a lumen configured to receive the control wire in a close fit.

4. The tissue grasping device of claim 3, wherein the inner sheath has a star-shaped transverse cross-section.

5. The tissue grasping device of claim 3, wherein the inner sheath is not attached to the helical coil.

6. The tissue grasping device of claim 1, wherein the control wire includes a visual indicator configured to indicate rotational movement of the control wire.

7. The tissue grasping device of claim 1, wherein the sheath lumen includes a proximal portion with a first inner diameter and a distal portion with a second inner diameter that is greater than the first diameter, wherein the helical coil is disposed within the distal portion of the sheath lumen.

8. The tissue grasping device of claim 7, wherein an outer diameter of the helical coil is greater than the inner diameter of the proximal portion.

9. The tissue grasping device of claim 1, wherein the control wire is devoid of any structure fixed to a proximal end face of the helical coil.

10. The tissue grasping device of claim 1, further comprising a heat-shrink tube disposed over at least a portion of the proximal region of the helical coil and at least a portion of the control wire adjacent the helical coil.

11. A tissue grasping device for use with an endoscope, comprising:
a sheath defining a sheath lumen, the sheath lumen having a proximal portion with a first inner diameter and a single step up to a distal portion with a second inner diameter that is greater than the first diameter;
a control wire slidably disposed within the sheath lumen, wherein the proximal region of the sheath lumen has a close fit over the control wire;
a helical coil disposed over and attached to a distal portion of the control wire, the helical coil including a proximal region in which adjacent windings are in contact, and a distal region in which adjacent windings are spaced apart, the helical coil having a sharpened distal tip, the helical coil slidably disposed within the distal portion of the sheath lumen, wherein an outer diameter of the helical coil is greater than the inner diameter of the proximal region, wherein the helical coil is slidable relative to the sheath from an undeployed configuration in which an entirety of the helical coil is disposed completely within the sheath lumen to a deployed configuration in which at least a distal portion of the helical coil extends distally beyond a distal end of the sheath; and
wherein the control wire is devoid of any structure fixed to a proximal end face of the helical coil.

12. The tissue grasping device of claim 11, wherein the helical coil is attached to the control wire with adhesive.

13. The tissue grasping device of claim 11, wherein the proximal region of the helical coil includes a first zone in which the adjacent windings are in contact, and a second zone proximal of the first zone, wherein adjacent windings in the second zone are spaced apart.

14. The tissue grasping device of claim 13, further comprising a connection element disposed within the second zone, the connection element configured to connect the helical coil to the control wire.

15. The tissue grasping device of claim 14, wherein the connection element is a weld.

16. The tissue grasping device of claim 11, wherein the control wire includes a visual indicator configured to indicate rotational movement of the control wire.

17. A tissue grasping device for use with an endoscope, comprising:
an outer sheath defining a sheath lumen;
a control wire slidably disposed within the sheath lumen;
an inner sheath slidably disposed within the sheath lumen, the inner sheath having a lumen configured to receive the control wire;
a tubular connector attached to a distal portion of the control wire; and
a helical coil disposed over and attached to the tubular connector such that the tubular connector is between an outer surface of the control wire and an inner surface of the helical coil, the helical coil including a proximal region in which adjacent windings are in contact, and a distal region in which adjacent windings are spaced apart, the helical coil having a sharpened distal tip, wherein the helical coil is slidable relative to the outer sheath from an undeployed configuration in which an entirety of the helical coil is disposed completely within the sheath lumen to a deployed configuration in which at least a distal portion of the helical coil extends distally beyond a distal end of the outer sheath;
wherein the tissue grasping device is devoid of any structures fixed to a proximal end face of the helical coil.

\* \* \* \* \*